(12) United States Patent
Cao

(10) Patent No.: US 12,071,459 B2
(45) Date of Patent: Aug. 27, 2024

(54) AMINO ACID SEQUENCE OF RECOMBINANT HUMAN BONE MORPHOGENETIC PROTEIN-2

(71) Applicant: ZHEJIANG RISING BIOTECHNOLOGY CO., LTD., Hangzhou (CN)

(72) Inventor: Jianxin Cao, Hangzhou (CN)

(73) Assignee: ZHEJIANG RISING BIOTECHNOLOGY CO., LTD., Hangzhou (CN)

( * ) Notice: Subject to any disclaimer, the term of this patent is extended or adjusted under 35 U.S.C. 154(b) by 132 days.

(21) Appl. No.: 17/717,120

(22) Filed: Apr. 10, 2022

(65) Prior Publication Data

US 2022/0315635 A1    Oct. 6, 2022

Related U.S. Application Data

(63) Continuation of application No. 16/518,378, filed on Jul. 22, 2019, now abandoned.

(30) Foreign Application Priority Data

Jul. 24, 2018 (CN) .......................... 201810818738.7

(51) Int. Cl.
| | | |
|---|---|---|
| C12N 15/63 | (2006.01) | |
| C07K 1/18 | (2006.01) | |
| C07K 14/51 | (2006.01) | |
| C12N 15/09 | (2006.01) | |
| C12N 15/66 | (2006.01) | |
| C07K 1/14 | (2006.01) | |
| C07K 1/16 | (2006.01) | |

(52) U.S. Cl.
CPC ............... C07K 14/51 (2013.01); C07K 1/18 (2013.01); *C07K 1/14* (2013.01); *C07K 1/16* (2013.01); *C12N 15/09* (2013.01); *C12N 15/63* (2013.01); *C12N 15/66* (2013.01)

(58) Field of Classification Search
None
See application file for complete search history.

(56) References Cited

U.S. PATENT DOCUMENTS

2013/0090290 A1*  4/2013  Qin ....................... C07K 14/51
                                                               435/68.1

OTHER PUBLICATIONS

Retnoningrum et al. (2012, Protein Expression and Purification 84:188-194).*

* cited by examiner

*Primary Examiner* — Elizabeth C. Kemmerer
(74) *Attorney, Agent, or Firm* — MUNCY, GEISSLER, OLDS & LOWE, P.C.

(57) ABSTRACT

The present invention relates to a field of biotechnology. It discloses a novel amino acid sequence of recombinant human bone morphogenetic protein-2 (rhBMP-2) and encoded nucleotide sequences thereof, and a method for preparing rhBMP-2. In the present invention, by further optimizing the nucleotide sequence of rhBMP-2, novel amino acid sequence of rhBMP-2 that can express good ectopic induced osteogenic activity and has good renaturation and purification effect is screened out. The engineered bacteria constructed by the present invention can induce the production of recombinant rhBMP-2 protein with an expression level of about 55%, and the produced target protein is more easily denatured and purified than the existing recombinant rhBMP-2, with better denaturation and purification effect and higher osteoinductive activity.

9 Claims, 8 Drawing Sheets

Specification includes a Sequence Listing.

AMINO ACID SEQUENCE OF RECOMBINANT HUMAN BONE MORPHOGENETIC PROTEIN-2

REFERENCE TO AN ELECTRONIC SEQUENCE LISTING

The content of the electronic sequence listing (04-10-2022_SeqList.txt; Size: 5,846 bytes; and Date of Creation: Apr. 10, 2022) is herein incorporated by reference in its entirety.

FIELD OF THE INVENTION

The present invention relates to a field of biotechnology, and in particular to a novel amino acid sequence of recombinant human bone morphogenetic protein-2 (rhBMP-2) and encoded nucleotide sequences thereof, and a method for preparing rhBMP-2.

BACKGROUND OF THE INVENTION

Bone morphogenetic protein (BMP) is a member of the transforming growth factor (TGF)-β superfamily. With unique osteoinductive activity, BMP has important functions in the repair of bone segment defects of bones and joints and spinal fusion, etc. At present, a variety of BMPs have been isolated from bone matrix of various animals such as cattle, pigs, sheep, rabbits, mice and human, etc., of which, human bone morphogenetic protein-2 (BMP-2) has the best induced osteogenic effect and it is an indispensable factor in the formation of the skeletal system. BMP-2 is an acidic glycoprotein containing 396 amino acid residues consisting of a N-terminal signal peptide, an intermediate propeptide and a C-terminal mature peptide. The mature peptide consists of 114 amino acids and is a part that exerts a function of osteogenic induction, which contains seven cysteine residues, of which 6 cysteine residues form an intramolecular disulfide bond and the other is used to form an intermolecular disulfide bond. The homodimer or heterodimer of the mature peptide is biologically active, wherein monomers form three pairs of disulfide bonds, forming a pair of interchain disulfide bonds between two monomers. The correct pairing of disulfide bonds has a direct impact on the biological activity and stability. In addition, a glycosylation site exists on the asparagine residue at position 55 of the mature peptide, but its biological activity is not affected by glycosylation. BMP-2 has been approved by the US FDA for bone injury, frontal repair, and spinal fusion. However, the source of fresh human bones is limited and bone BMP-2 level is low in the bone, only 1-2 μg per kg of cortical bone, which is difficult to meet clinical needs. Moreover, its extraction process is complicated, and its purity and activity could not be guaranteed. Therefore, it has become a research hotspot to produce this protein by genetic recombinant expression using the genetic engineering techniques.

Currently, rhBMP-2 is prepared mainly through eukaryotic expression vector and prokaryotic expression vector. Eukaryotic expression systems are mainly used at abroad, such as CHO, COS and baculovirus systems. Most eukaryotic expression products are secretory type and undergo glycosylation processing; rhBMP-2 is a secretory protein and has glycosylation sites, so the eukaryotic expression system is an ideal expression system. The product prepared by a eukaryotic expression system has high activity, but it has the drawbacks of low expression level, high production cost, and unsuitable for mass production, etc. At present, medical rhBMP-2 at home and abroad is mainly produced by a prokaryotic expression system with *Escherichia coli* as a host, to obtain fragments with different lengths of rhBMP-2 mature peptides. As prokaryotic expression systems do not have the process of post-translational modification of polypeptide chains by eukaryotic cells, the eukaryotic gene proteins cannot be correctly folded and post-translationally processed (such as forming disulfide bonds, glycosylation, polymerization, protease degradation, etc.), which restricts their biological activity and availability. In addition, eukaryotic proteins expressed in prokaryotic expression systems usually aggregate into insoluble inclusion bodies in the cytoplasm of bacteria in an inactive manner, which must undergo denaturation, renaturation to restore their natural activities. Chinese invention patent CN1215171C discloses a method for producing a truncated recombinant human bone morphogenetic protein-2 mature peptide, which is a synthetically encoded BMP-2 nucleotide sequence with 107 amino acid residues in C-terminal, an initiation codon ATG is added before the first amino acid codon and the second amino acid arginine (R) is mutated to a lysine (K) residue, with amino acid sequence of MKKLKSSCKR HPLYVDFSDV GWNDWIVAPP GYHAFYCHGE CPFPLADHLN STNHAIVQTL VNSVNSKIPK ACCVPTELSA ISMLYLDENE KVVLKNYQDM VVEGCGCR (SEQ ID No: 6). The amount of human truncated BMP-2 produced by genetically engineered bacteria is 30-50% of the total soluble protein of the bacteria, with osteogenic activity. Chinese invention patent CN101787369B discloses an optimized recombinant human bone morphogenetic protein-2 DNA sequence and the preparation and use of encoded protein thereof. In the invention, by optimizing DNA sequence, rhBMP-2 with complete mature peptide (114 amino acid residues) is obtained, and the product purity exceeds 95%, after purification, the yield of dimer is about 21%. The prepared rhBMP-2 using the existing several kinds of rhBMP-2 mature peptide fragments has poor renaturation and purification effects, and the final product has low biological activity. To solve the above problems, it is required to analyze the mature peptide gene using genetic recombination technology, optimize the nucleotide sequence of the target gene without affecting and changing the molecular structure of proteins, and screen out novel amino acid sequence of rhBMP-2 that can express good ectopic induced osteogenic activity and has good renaturation and purification effect.

SUMMARY

An object of the present invention is to provide a novel amino acid sequence of recombinant human bone morphogenetic protein-2 (rhBMP-2) such that the expressed protein has good renaturation and purification effect and has high biological activity and bone repair ability.

In order to solve the above technical problems, the present invention adopts the following technical solutions.

The amino acid sequence of rhBMP-2 is optimized and the novel amino acid sequence of recombinant human bone morphogenetic protein-2 is as follows:

```
                                        (SED ID No: 1)
KRLK SSCKR HPLYV DFSDV GWNDW IVAPP GYHAF YCHGE

CPFPL ADHLN STNHA IVQTL VNSVN SKIPK ACCVP TELSA

ISMLY LDENE KVVLK NYQDMVVEGC GCR.
```

Further, the N-terminal of the above protein sequence is added with methionine M encoded by the initiation codon (AUG). The amino acid sequence is as follows:

```
                                            (SED ID No: 2)
MKRLK SSCKR HPLYV DFSDV GWNDW IVAPP GYHAF YCHGE

CPFPL ADHLN STNHA IVQTL VNSVN SKIPK ACCVP TELSA

ISMLY LDENE KVVLK NYQDM VVEGC GCR.
```

The amino acid sequence also includes that modified by glycosylation, for example, amino acid sequences modified by PEG.

By optimizing the codons, all rare codons are removed to become *E. coli*-preferred codons. The optimized DNA sequences are as follows:

```
                                            (SED ID No: 3)
ATGAAACGTCTGAAAAGCAGCTGCAAACGTCACCCGCTGTACGTTGATTT

CAGCGATGTTGGCTGGAACGATTGGATCGTTGCGCCGCCGGGCTACCACG

CGTTCTACTGCCACGGCGAATGCCCGTTCCCGCTGGCGGATCACCTGAAC

AGCACCAACCACGCGATCGTTCAGACCCTGGTTAACAGCGTTAACAGCAA

AATCCCGAAAGCGTGCTGCGTTCCGACCGAACTGTCTGCGATCTCAATGC

TGTACCTGGATGAAAACGAAAAAGTTGTTCTGAAAAACTACCAGGATATG

GTTGTTGAAGGTTGCGGTTGCCGTTAA.
```

Another object of the present invention is to provide a method for producing recombinant human bone morphogenetic protein-2, comprising the following steps: (1) designing an amino acid sequence and a DNA sequence encoding recombinant human bone morphogenetic protein-2; (2) constructing an expression vector to transform *E. coli* host cells; (3) screening positive clones for culture and inducing the expression of the target protein; (4) renaturing and purifying the expression product to obtain the recombinant human bone morphogenetic protein-2.

Preferably, the vector is expressed in eukaryotic cells, for example CHO cells. The expressions of protein modified by glycosylation in eukaryotic cells and the amino acid sequence with activity after modified by glycosylation are also within the scope of the present invention. Alternatively, the protein is artificially modified in vitro, for example, modified with PEG, to greatly increase its stability. Our experiments have found that the stability of the modified proteins that are expressed in vitro is increased by about 35-50% after artificial modification.

Preferably, a dilution method is used for renaturation and the final concentration of the protein in the renaturation buffer is controlled at 0.05-0.5 mg/ml.

Preferably, in step (4), multi-step ion exchange chromatography is used for purification, and the steps are as follows: (1) loading the renatured recombinant human bone morphogenetic protein-2 solution onto a well-balanced strong anion column, and rinsing with equilibration buffer A to reach the baseline after loading; (2) performing stepwise salt-gradient elution using the elution buffer A and collecting the main peak; (3) mixing the target peak solution collected from the strong anion column and loading onto a weak cation column, and rinsing with equilibration buffer B to reach the baseline after loading; (4) performing stepwise salt-gradient elution using the elution buffer B and collecting the main peak.

Preferably, the equilibration buffer A comprises 10-50 mM Tris-HCl, 1-5 M urea, 1%-10% mannitol, pH 8.5-8.9; the elution buffer A comprises 10-50 mM Tris-HCl, 1-5 M urea, 1%-10% mannitol, 1-5 M NaCl, pH 8.5-8.9; the equilibration buffer B comprises 10-50 mM phosphate buffer PB, 1-5M urea, 1%-10% mannitol, pH 6.0-6.5; and the elution buffer B comprises 10-50 mM phosphate buffer PB, 1-5M urea, 1%-10% mannitol, 1-5 M NaCl, pH 6.0-6.5.

In the present invention, by optimizing the nucleotide sequence of rhBMP-2 gene to screen out a novel amino acid sequence capable of expressing rhBMP-2 with good ectopic osteoinductive activity and good renaturation and purification effect. The engineered bacteria constructed by the invention can induce the production of recombinant rhBMP-2 protein with an expression level of about 55%, and the produced target protein is more easily denatured and purified than the existing recombinant rhBMP-2, with better denaturation and purification effect. The yield of purified target protein is greater than 60% or about 60% and the purity is higher than 98%. The expressed recombinant rhBMP-2 has higher osteoinductive activity, presenting broad market prospect.

DETAILED DESCRIPTION

The present invention is further described in conjunction with particular embodiments, which are merely illustrative of the invention, but are not intended to limit the invention. Unless otherwise indicated, the terms used herein have the same meaning as commonly understood by those skilled in the art.

In the present invention, all percentages are expressed in weight/weight (w/w) unless otherwise specified. All equipment and materials are commercially available or commonly used in the industry. Unless otherwise specified, the method used in the embodiments is a general technology in the art. Since the codon (ATG) of methionine M is the initiation codon of protein translation process, the amino acid sequence SEQ ID No: 2 containing the methionine M at the N-terminal is used for experiments.

Example 1 Design of Novel Amino Acid Sequence of rhBMP-2 and Construction of Recombinant rhBMP-2 Expression Vector 1. The Novel Amino Acid Sequence Encoding rhBMP-2 is Designed as Follows:

(SED ID No: 1)
KRLK SSCKR HPLYV DFSDV GWNDW IVAPP GYHAF YCHGE

CPFPL ADHLN STNHA IVQTL VNSVN SKIPK ACCVP TELSA

ISMLY LDENE KVVLK NYQDM VVEGC GCR

Further, the N-terminal of the above amino acid sequence is added with methionine M encoded by the initiation codon (ATG). The amino acid sequence is as follows:

(SED ID No: 2)
MKRLK SSCKR HPLYV DFSDV GWNDW IVAPP GYHAF YCHGE

CPFPL ADHLN STNHA IVQTL VNSVN SKIPK ACCVP TELSA

ISMLY LDENE KVVLK NYQDM VVEGC GCR

Further, by optimizing the codons, all rare codons are removed to become *E. coli*-preferred codons, at the same time, the restriction site BamHI (GGATCC) is added at the terminal. The optimized DNA sequences are as follows:

(SEQ ID NO: 3)
ATGAAACGTCTGAAAAGCAGCTGCAAACGTCACCCGCTGTACGTTGATTT

CAGCGATGTTGGCTGGAACGATTGGATCGTTGCGCCGCCGGGCTACCACG

CGTTCTACTGCCACGGCGAATGCCCGTTCCCGCTGGCGGATCACCTGAAC

AGCACCAACCACGCGATCGTTCAGACCCTGGTTAACAGCGTTAACAGCAA

AATCCCGAAAGCGTGCTGCGTTCCGACCGAACTGTCTGCGATCTCAATGC

TGTACCTGGATGAAAACGAAAAAGTTGTTCTGAAAAACTACCAGGATATG

GTTGTTGAAGGTTGCGGTTGCCGTTAA.

Figure 1:
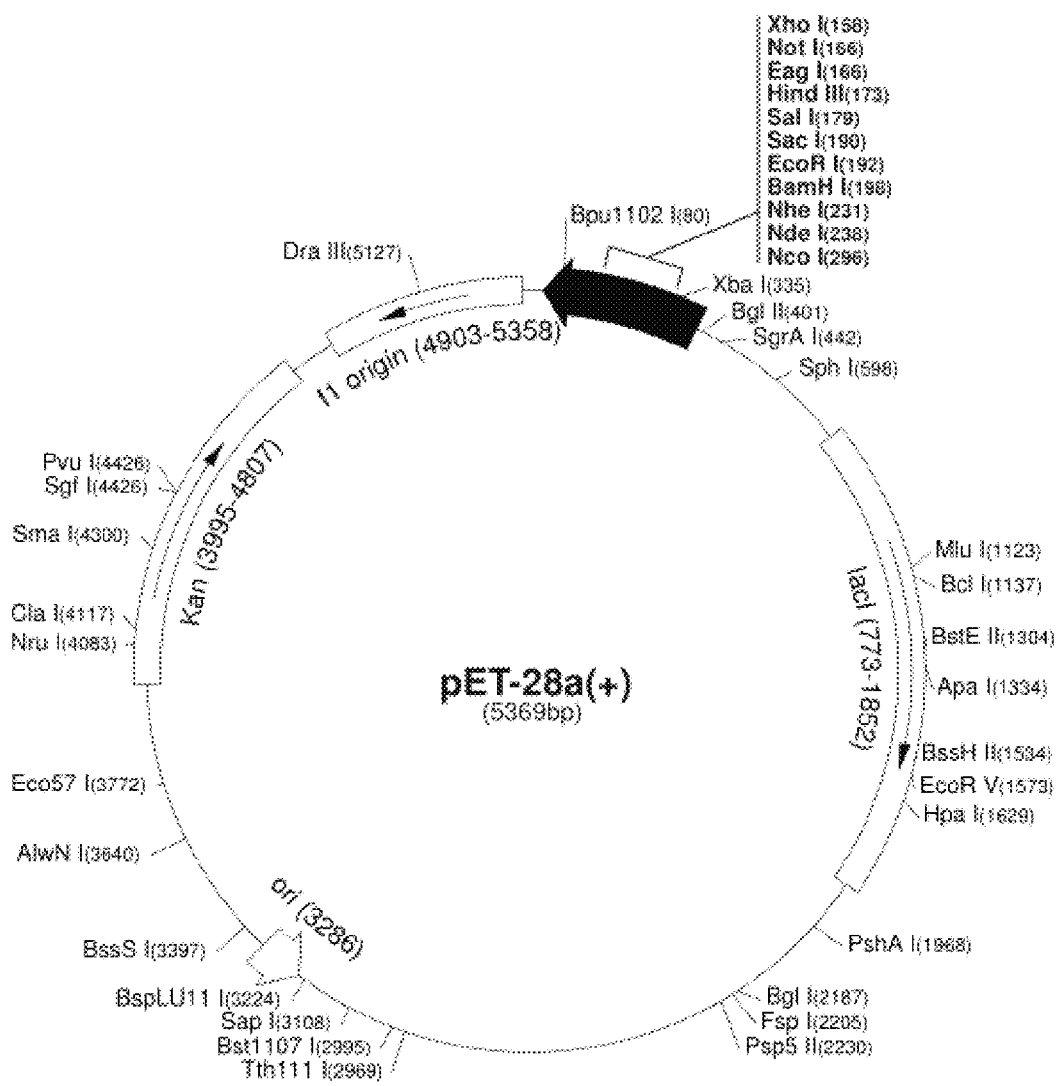
FIG. 1 is a profile of pET28 plasmid used in the present invention.

2. Construction of Expression Vector, Transformation of Host Cells of *Escherichia coli*, Construction of Expression Engineering Bacteria and Process of Recombinant Protein Expression The prokaryotic expression vector pET28a was selected as the expression vector of recombinant rhBMP-2 protein, and the plasmid map of pET28a was shown in FIG. 1. The gene fragments described in SEQ ID No: 3 were inserted into an expression vector after digestion to complete the construction of vector. The pET28a vector had a T7lac promoter, T7 could ensure efficient expression of the exogenous inserted gene, and the lac lactose operon enabled the gene to maintain a low background expression in the absence of an inductive agent. The multiple cloning sites of the pET28a vector are publicly available.

(1) Construction of an Expression Vector

The pET28a vector was digested with NcoI and filled in, and then digested with BamHI. At the same time, the synthesized rhBMP-2 (SEQ ID NO: 3) was digested with BamHI. The reaction system: total reaction volume 20 μL, ddw 12 μL, plasmid DNA 5 μL, 10× Buffer K2 μL, BamHI 1 μL.

The digested plasmid was separated on 1% agarose gel, and the target fragments were cleaved from the gel, and target fragments were recovered using Axygen's gel recovery kit.

After recovering DNA fragments, the pET28a vector fragment and the rhBMP-2 gene fragment were ligated with T4 DNA ligase. The ligation reaction system was: total reaction volume 10 μL, pET28a 4 μL, rhBMP-2 4 μL, 10×DNA ligase Buffer 1 μL, T4 DNA ligase 1 μL. The ligation reaction was carried out at 16° C. for 1 hour.

(2) Transformation of *Escherichia coli* Host Cells

After the ligation reaction was completed, the recombinant plasmid was transformed into *E. coli* DH5a cells by heat shock transformation. The transformation process was as follows: the ligation product was added to *E. coli* competent cells, placed on ice for 30 min, then the competent cells were placed in a 42° ° C. water bath for heat shock for 90 sec, and then a centrifuge tube was quickly inserted into the ice, after 1-2 min, 1 mL of LB medium was added, and the centrifuge tube was placed in a shaker and incubated for 1 hour at 37° C. and 160 rpm. *Escherichia coli* was collected by centrifugation and coated to a kanamycin-containing LB solid medium, and a plate was placed in a 37° C. biochemical incubator for culture overnight. On the next day, a single clone was picked and PCR was used to identify whether a foreign gene was inserted. The PCR reaction system was: total reaction volume 20 μL, ddw 9 μL, 2 × Taq pre-mix 10 μL, T7 promoter (10 μM) 0.5 μL, rhBMP-2 reverse primer (10 μM) 0.5 μL.

The cells of partially picked monoclonal colonies were taken and added to the PCR reaction system for PCR reaction on a Bio-Rad PCR instrument. The reaction procedure was as follows: pre-denaturation at 94 °C for 5 min; denaturation at 94 °C for 30 sec, annealing at 55° C. for 30 sec, extension at 72° C. for 30 sec, after 35 cycles, extension at 72°C for 15 min.

The correct monoclone identified by PCR was sequenced with T7promoter primers to detect the correctness of the rhBMP-2 sequence. The correctly sequenced monoclone was re-inoculated into a kanamycin-containing LB medium, and cultured in a shaker at 37° ° C., 250 rpm, and then the plasmid was extracted for use. The recombinant plasmid was named pET28a-rhBMP-2.

(3) Transformation of rhBMP-2 Expression Vector into *E. coli* Expression Strain The recombinant rhBMP-2 protein was expressed by BL21 (DE3) expression strain. The recombinant plasmid pET28a-rhBMP-2 was added to *E. coli* BL21 (DE3) competent cells, placed on ice for 30 minutes, and the water bath was heated to 42° C. for use. After placed on ice for 30 min, the centrifuge tube containing *Escherichia coli* BL21 (DE3) was placed in a 42° C. water bath for heat shock for 90 sec, and then a centrifuge tube was quickly inserted into the ice, after 1-2 min, 1 mL of LB medium was added, and the centrifuge tube was placed in a shaker for culture for 1 hour at 37° C. and 160 rpm. *Escherichia coli* BL21 (DE3) was collected by centrifugation and coated to a kanamycin-containing LB solid medium, and a plate was placed in a 37° C. biochemical incubator for culture overnight. On the next day, a single clone was picked and PCR was used to identify whether BL21(DE3) was transferred to the recombinant plasmid. The PCR reaction system was: total reaction volume 20 μL, ddw 9 μL, 2 × Taq pre-mix 10 μL, T7 promoter (10 μM) 0.5 μL, rhBMP-2 reverse primer (10 μM) 0.5 μL.

The cells of partially picked monoclonal colonies were taken and added to the PCR reaction system for PCR reaction on a Bio-Rad PCR instrument. The reaction procedure was as follows: pre-denaturation at 94 °C for 5 min; denaturation at 94° C. for 30 sec, annealing at 55° C. for 30 sec, extension at 72° C. for 30 sec, after 35 cycles, extension at 72° ° C. for 15 min.

The correct monoclone identified by PCR was transferred to a kanamycin-containing LB medium, and cultured in a shaker at 37° C. and 250 rpm. When the OD600 of the bacteria solution reaches 0.6-0.8, the bacteria solution was taken out and 80% sterile glycerol was added to a final concentration of 10%, and then stored at −20° ° C. for later use.

(4) Expression of Recombinant rhBMP-2

Figure 2:
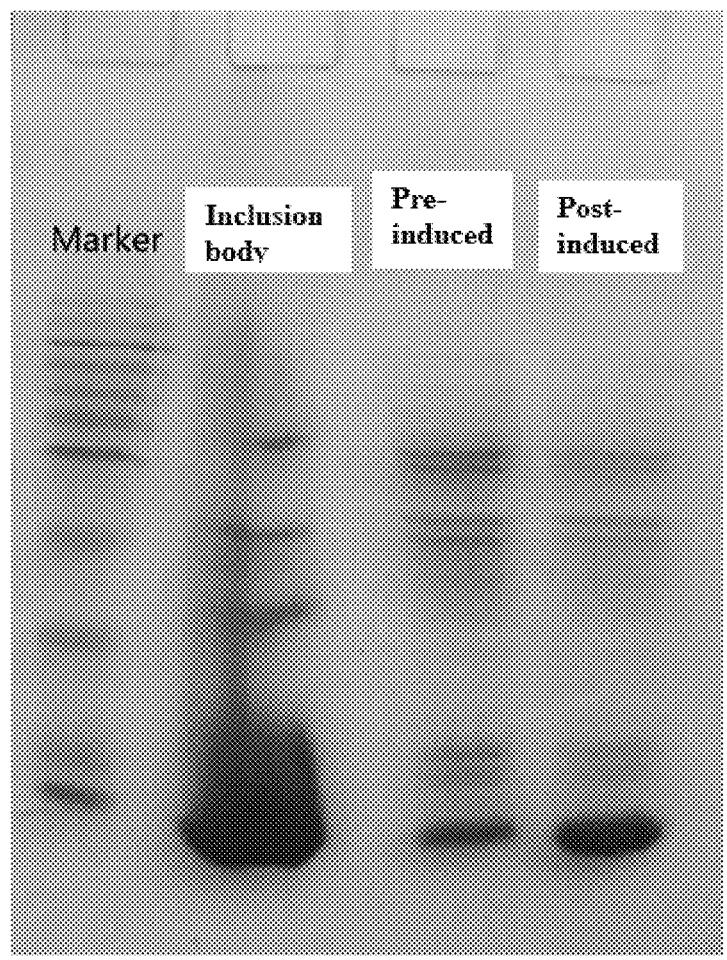
FIG. 2 is a SDS-PAGE electrophoresis pattern of rhBMP-2 induced expression.

The BL21 (DE3) strain containing pET28a-rhBMP-2 stored in glycerin was inoculated into a kanamycin-containing LB liquid medium at a volume ratio of 1:1000, and shake-flask cultured to the logarithmic phase at the condition of 37° C. and 100-200 rpm. The induced expression of rhBMP-2 protein was performed by different concentrations of inductive agent IPTG at different induction times and different induction temperatures. After the induction culture, the solution was centrifuged for 20 min at 3500 rpm and 4° ° C. to collect the thallus, and then the protein expression level was analyzed by SDS-PAGE. The combination with highest expression of rhBMP-2 was selected as the experimental parameters with the optimized induction expression of rhBMP-2 protein. The experiments showed that, the protein expression level was highest (about 55%) when the IPTG concentration was 1.0 mM, the induction temperature was 37° C. and the induction time was 5 h (FIG. 2).

Example 2 Renaturation and Purification of Recombinant rhBMP-2

(1) Renaturation

After the bacteria were disrupted by sonication, the inclusion bodies formed by the rhBMP-2 protein were extracted, then the inclusion bodies were washed, and dissolved with a denaturant guanidine hydrochloride. The renaturation was carried out by the dilution method, and the final concentration of the renaturation liquid protein was controlled at 0.05-0.5 mg/ml. The rhBMP-2 denatured protein solution was continuously and slowly added to the renaturation butter for dilution and renaturation. After addition, the mixture was slowly stirred for a few minutes, and allowed to stand for 2-20 days for renaturation. After renaturation, the rhBMP-2 mature peptide monomer forms a dimer, and all monomers form three pairs of intramolecular disulfide bonds, and two monomers form a dimer through an intermolecular disulfide bond. After renaturation, samples were taken for SDS-PAGE electrophoresis, to judge the renaturation rate and renaturation effect.

Figure 3:
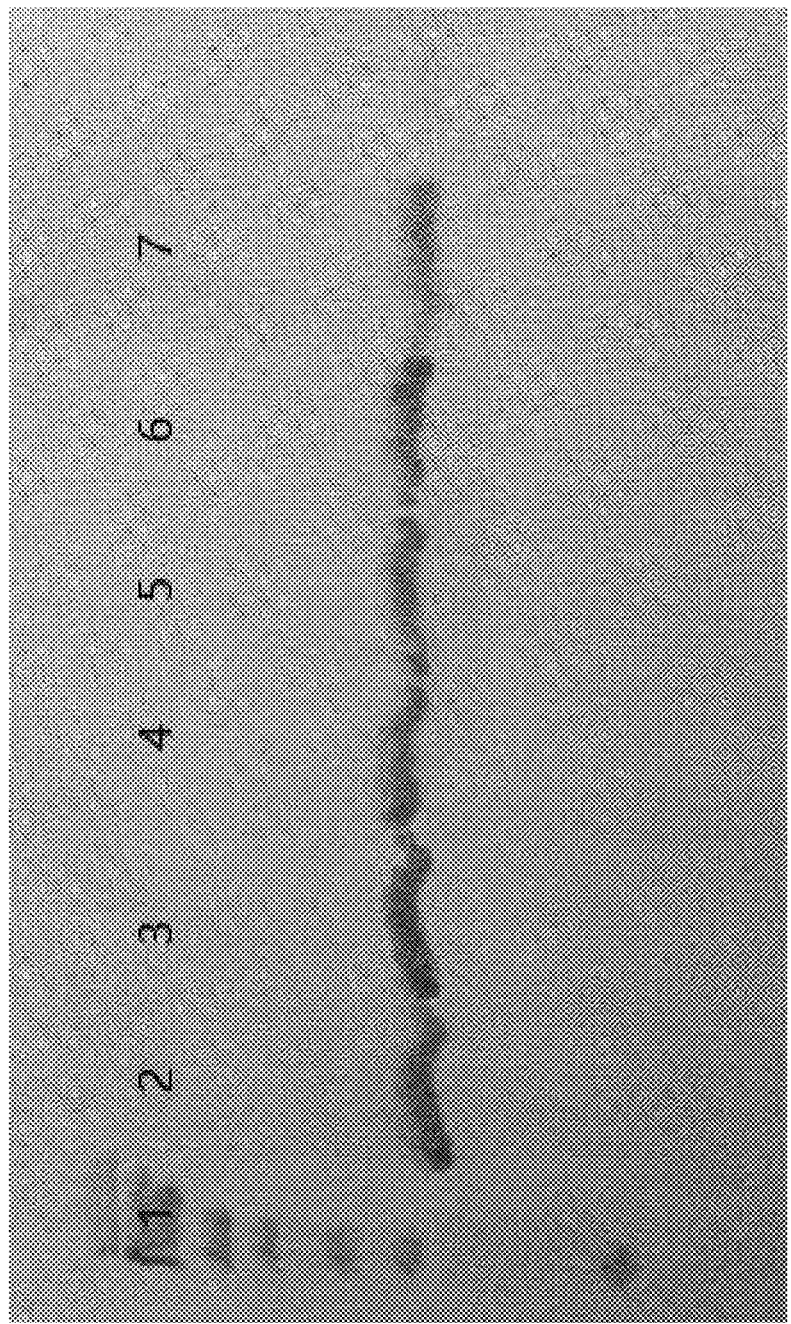
FIG. 3 is a renaturation result of SDS-PAGE electrophoresis analysis, wherein 1: molecular weight standard; 2-7: renatured rhBMP-2 dimer.

According to the results of FIG. 3, 150.2 mg of the inclusion body protein was obtained by 500 mL of induced bacterial solution, and the yield of target protein rhBMP was high (about 80%).

(2) Purification

Figure 4A:
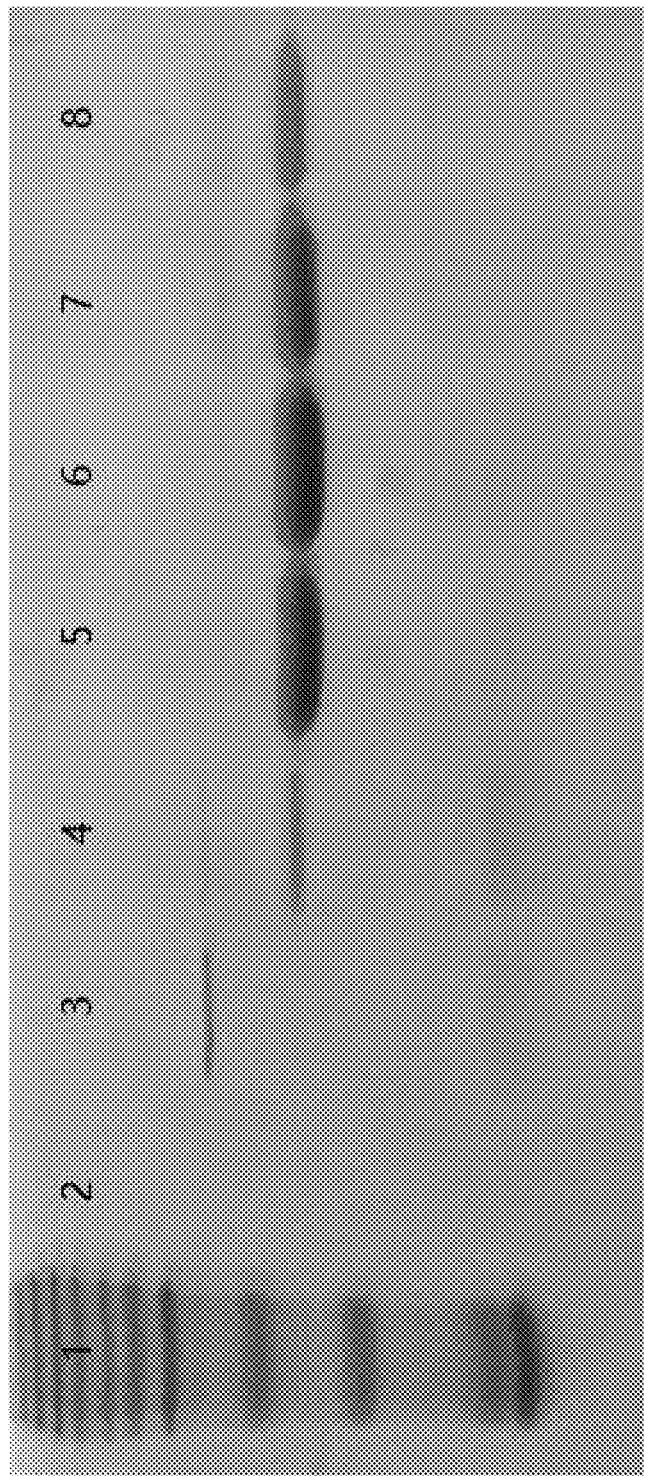
FIG. 4 is a purity result of SDS-PAGE electrophoresis analysis, wherein A is a target peak electrophoresis pattern in strong anion column, B is a target peak electrophoresis pattern in weak cation column, 1: molecular weight standard; 2-10: collected target peaks.

The multi-step ion exchange chromatography was used for purification and the specific purification steps were as follows:

1) The renatured rhBMP-2 solution was loaded onto a well-balanced strong anion column, and then rinsed with equilibration buffer A to reach the baseline after loading. The equilibration buffer A comprised 10-50 mM Tris-HCl, 1-5 M urea, 1%-10% mannitol, pH 8.5-8.9.
2) A stepwise salt-gradient elution was performed using the elution buffer A and the main peak was collected for SDS-PAGE analysis (FIG. 4A). The elution buffer A comprised 10 −50 mM Tris-HCl, 1-5 M urea, 1%-10% mannitol, 1-5 M NaCl, pH 8.5-8.9.
3) The target peak solution collected from the strong anion column was mixed and loaded onto a weak cation column, and then rinsed with equilibration buffer B to reach the baseline after loading. The equilibration buffer B comprised 10-50 mM phosphate buffer PB, 1-5M urea, 1%-10% mannitol, pH 6.0-6.5.
4) A stepwise salt-gradient elution was performed using the elution buffer B and the main peak was collected for SDS-PAGE analysis. The elution buffer B comprised 10-50 mM phosphate buffer PB, 1-5M urea, 1%-10% mannitol, 1-5 M NaCl, pH 6.0-6.5.

Figure 4B:
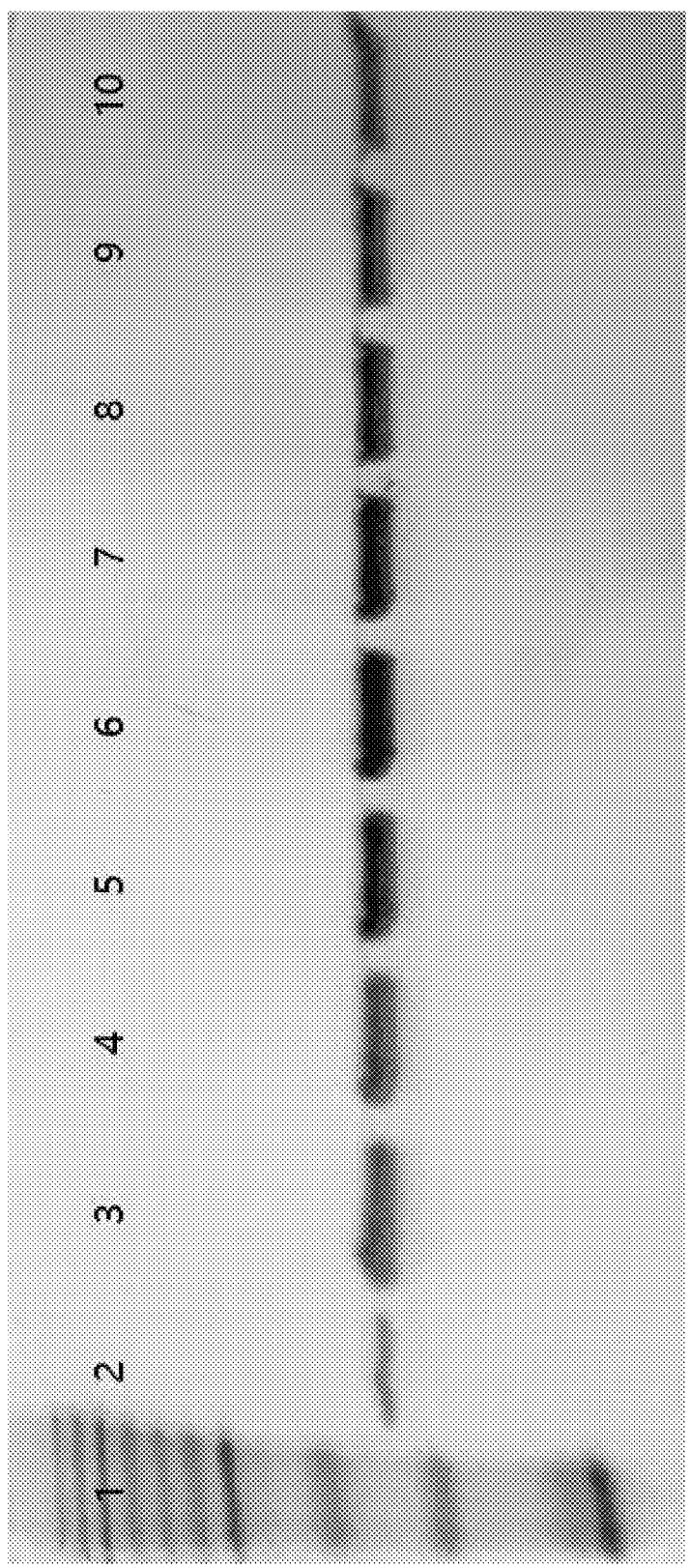

FIG. 4B showed that the target protein recovered was a single band with purity higher than 98%. Data analysis showed that the total soluble protein of the renaturation solution was 150.2 mg, and the yield of purified rhBMP-2 was 89.3 mg, with a yield rate of about 60%.

Figure 5:
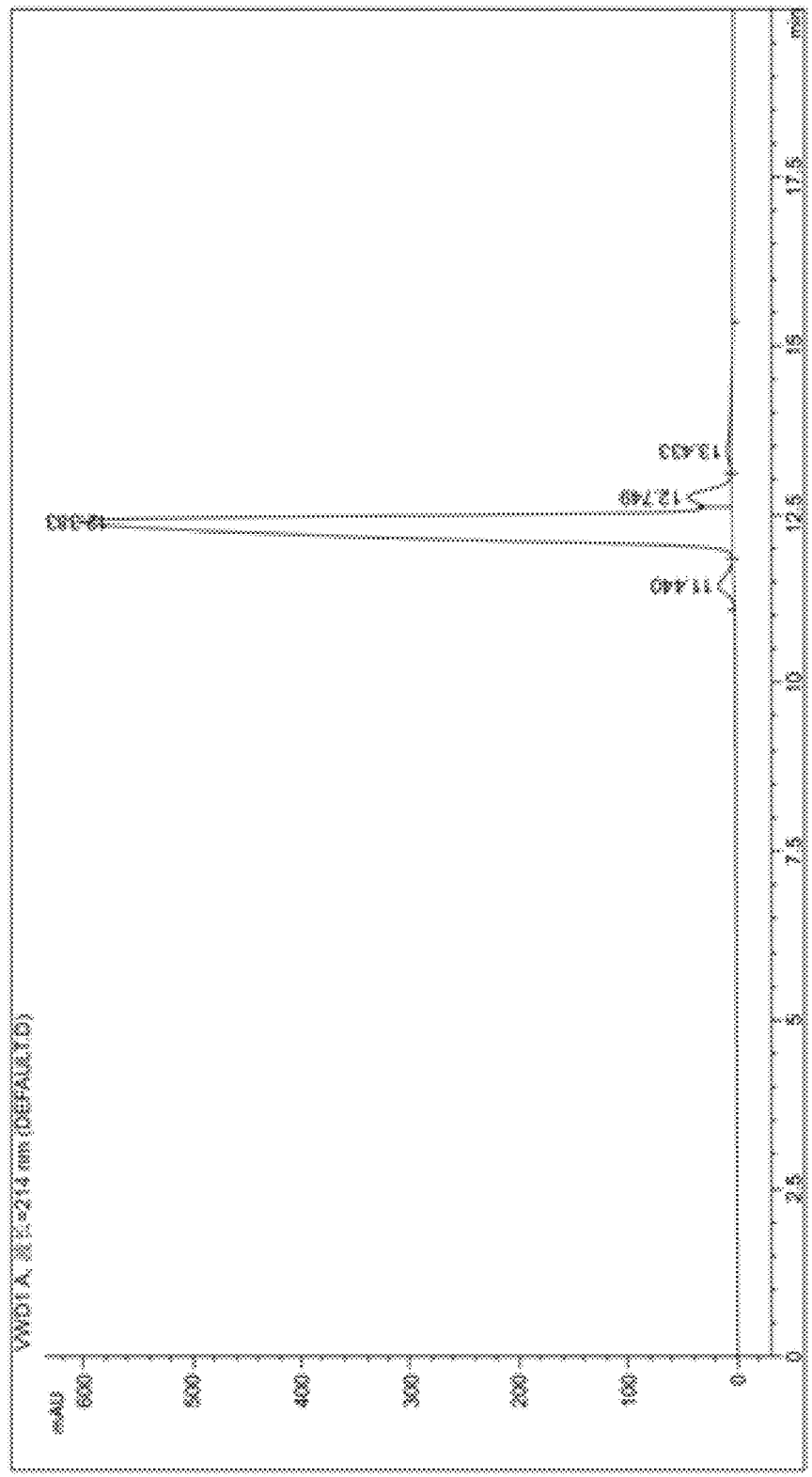
FIG. 5 is a capillary electrophoresis purity analysis pattern of rhBMP-2, detected at UV214 nm.

The capillary electrophoresis analysis showed that the sample purity was 98.5% (FIG. 5).

Example 3 In Vitro Activity Assay of Recombinant rhBMP-2 in C2C12 Cells

C2C12 cells (mesenchymal stem cells) were cultured in DMEM high glucose medium (containing 10% fetal bovine serum, 100 U/mL penicillin and 100 g/mL streptomycin) under the conditions of 37° C. and 5% $CO_2$ and digested with 0.25% trypsin for passage every 1-2d. C2C12 cells were inoculated in a 24-well plate, and when cell fusion reached around 30%, recombinant rhBMP-2 was added for continuous culture. After 5 days of culture, the medium was discarded and washed twice with pre-cooled PBS buffer. After lysed with lysate for 5 min, the supernatant was centrifuged and the activity of alkaline phosphatase (ALP) was quantitatively determined according to the instructions of the kit.

Controlled Trial:

In order to compare the biological activities of recombinant rhBMP-2 expressed by the novel amino acid sequences of the present invention, three kinds of reported polypeptides were used for controlled trial. The engineered bacteria were constructed according to the reported amino acid sequences and gene sequences and the corresponding recombinant rhBMP-2 was obtained by induced expression, renaturation and purification using the method described herein. The amino acid sequences of the three polypeptides selected were as follows.

1. 115-peptide (containing methionine in the N terminal, disclosed in the invention patent CN101787369B)

```
                                       (SEQ ID No: 4)
MQAKHKQRKR LKSSCKRHPL YVDFSDVGWN DWIVAPPGYH

AFYCHGECPF PLADHLNSTNHAIVQTLVNS VNSKIPKACC

VPTELSAISM LYLDENEKVV LKNYQDMVVE GCGCR
```

2. 109-peptide (containing methinonine in the N terminal)

```
                                       (SEQ ID No: 5)
MRKRLKSSCK RHPLYVDFSD VGWNDWIVAP PGYHAFYCHG

ECPFPLADHL NSTNHAIVQTLVNSVNSKIP KACCVPTELS

AISMLYLDEN EKVVLKNYQD MVVEGCGCR
```

3. 108-peptide (containing methionine in the N terminal, disclosed in the invention patent CN1215171C)

(SEQ ID No: 6)
MKKLKSSCKR HPLYVDFSDV GWNDWIVAPP GYHAFYCHGE

CPFPLADHLN STNHAIVQTLVNSVNSKIPK ACCVPTELSA

ISMLYLDENE KVVLKNYQDM VVEGCGCR

4. The sequences designed in the present invention (containing methionine in the N terminal)

(SED ID No: 2)
MKRLK SSCKR HPLYV DFSDV GWNDW IVAPP GYHAF YCHGE

CPFPL ADHLN STNHA IVQTL VNSVN SKIPK ACCVP TELSA

ISMLY LDENE KVVLK NYQDM VVEGC GCR

Compared with the 115-peptide, the amino acid sequence of the present invention was a 107 amino acid sequences truncated from amino acid residues of the rhBMP-2 mature peptide; 109-peptide was 108 amino acid sequences truncated from amino acid residues of the rhBMP-2 mature peptide; and 108-peptide was a 107 amino acid sequences truncated from amino acid residues of the rhBMP-2 mature peptide and the second amino acid arginine residue (R) was mutated to a lysine residue (K).

The test results were shown in the table below.

TABLE 1

Activity assay in C2C12 cells

| Experiment group | ALP activity |
| --- | --- |
| 115-peptide | 43% |
| 109-peptide | 45% |
| 108-peptide | 78% |
| The present invention | 98% |

The above results showed that the activity of recombinant rhBMP-2 expressed by the amino acid sequence of the present invention was much higher than that of the other three kinds of peptide in the C2C12 cells, indicating that the C2C12 cells could be better differentiated to osteoblasts under the action of recombinant rhBMP-2 designed in the present invention.

Some researchers believe that the closer the length of rhBMP-2 to a complete mature peptide, the better the osteogenic activity (Lin Song et al., Acta Biochimica et Biophysica Sinica, 1996, 28(1): 8). In the present invention, it was surprisingly found that the truncated polypeptide of the present invention had much higher activity to promote differentiation of C2C12 cells than mature peptides, possibly because the peptide chain of the mature peptide was longer and the peptide chain was liable to form a helical structure under the action of hydrogen bonds so that the active site on the peptide chain was easily embedded in the hydrophobic cavity, affecting its binding to the receptor on the cell membrane surface, and the shortened peptide chain would reduce the effect of steric hindrance; another reason may be that the nitrogen-terminal peptide segment of the mature peptide had no activity, or the nitrogen-terminal peptide segment of the mature peptide had endoprotease activity, which would cause degradation of rhBMP-2 and affect its activity. The specific reasons need to be further identified.

The 109-peptide was 108 amino acid sequences truncated from amino acid residues of the rhBMP-2 mature peptide. Compared with the present invention, its peptide chain nitrogen terminal contained one more arginine residue (R). Experiments have found that its activity to promote the differentiation of C2C12 cells is significantly lower than that of the present invention, possibly because the presence of the arginine residue at position 108 of the mature peptide would cause the degradation of rhBMP-2. Further, compared with the present invention, the second amino acid arginine residue (R) of peptide chain of the disclosed 108-peptide was mutated to a lysine residue (K), which would reduce the activity of the recombinant protein, thus, it could be inferred that the mutation of the arginine residue at position 106 of the mature peptide of rhBMP-2 would affect its biological activity.

Example 4 Effect of Three Vectors on Mouse Muscle Ectopic Osteogenesis Induced by Recombinant RhBMP-2

The recombinant rhBMP-2 aqueous solution was mixed with high-concentration gelatin, chitosan or natural coral, and the recombinant rhBMP-2 was uniformly combined with the three vectors to form a composite material by vacuumizing. Each vector contained 100 μg rhBMP-2, which was lyophilized and disinfected by ethylene oxide for later use.

Six normal ICR male mice were randomly divided into three groups, two mice in each group. After anesthesia with 1% sodium pentobarbital, the hind limbs were depilated and disinfected, and the skin was cut to separate the spatium intermusculare, and then implanted with a certain amount of the above composite material. Among them, the implanted materials in the first group used high concentration gelatin as a vector, and chitosan was used as a vector in the second group, and natural coral was used as a vector in the third group. Mice were given antibiotics to prevent infection, and then muscles and skin were sutured layer by layer, and the wounds were disinfected for normal feeding. Three weeks after the implantation experiment, the mice underwent radiological examination (X-ray) to observe if bone tissues appeared in the hind limbs of the mice. The mice were sacrificed, bone tissues of the implanted area were taken out, and the bones contained were weighed.

The radiological examination showed that the ectopic osteogenesis of the first group of mice was obvious with tight adhesion to autologous bone of mice. Further bone weighing found that, the average bone weight was 0.706 g when a high concentration of gelatin was used as the vector; the average bone weight was 0.266 g when chitosan was used as the vector; and the average bone weight was 0.345 g when the natural coral was used as the vector. The above results showed that, a high-concentration of gelatin could promote ectopic osteogenesis, possibly because the molecular structure of gelatin was more suitable for osteogenesis, so that rhBMP-2 was in uniform contact with adjacent tissues, to continuously maintain its activity and prolong the reaction time.

Example 5 Mouse Muscle Ectopic Osteogenesis Induced by Four Kinds of Recombinant rhBMP-2

In order to compare the biological activity of recombinant rhBMP-2 of the novel amino acid sequence of the present invention, the inventors conducted controlled trial using the recombinant rhBMP-2 of three kinds of reported polypeptides described in Example 3 (the recombinant protein was prepared according to the method described in the present invention). In the experiments, a high-concentration gelatin was used as a vector to form a composite material with four kinds of rhBMP-2. Each kind of composite material contained 100 μg of corresponding rhBMP-2.

Eight normal ICR male mice were randomly divided into four groups, two mice in each group. After anesthesia with 1% sodium pentobarbital, the hind limbs were depilated and disinfected, and the skin was cut to separate the spatium intermusculare, then implanted with a certain amount of the above four kinds of composite material. Three weeks later, radiological examination (X-ray) and osteogenesis testing were performed.

Figure 6A:
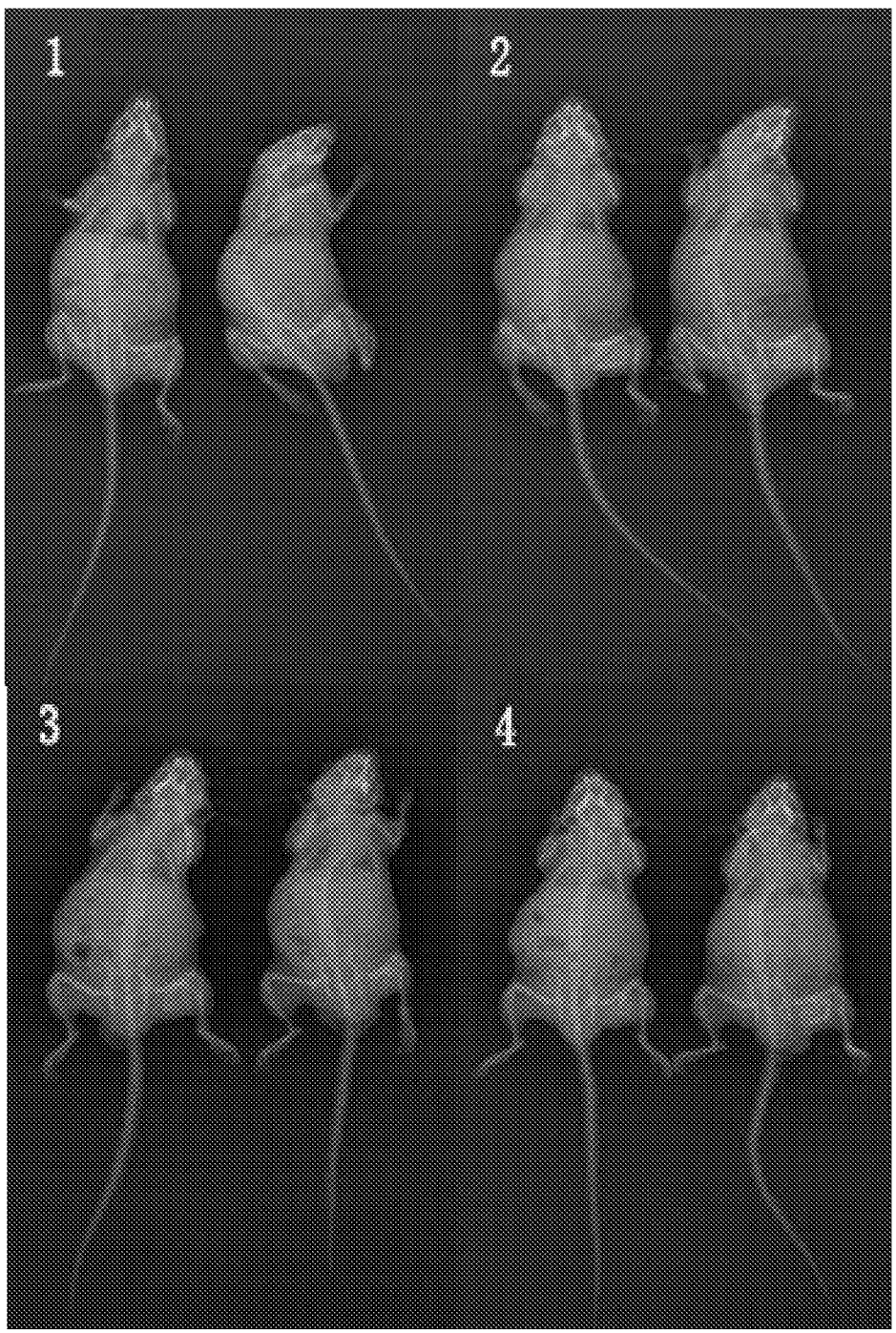
FIG. 6 shows mouse muscle ectopic osteogenesis radiology examination of rhBMP-2 and induced new bones, wherein, 1 is an induced osteogenic effect chart of 108-peptide recombinant rhBMP-2, 2 is an induced osteogenic effect chart of rhBMP-2 expressed by amino acid sequences in the present invention, 3 is an induced osteogenic effect chart of 109-peptide recombinant rhBMP-2, 4 is an induced osteogenic effect chart of 115-peptide recombinant rhBMP-2.
Figure 6B:
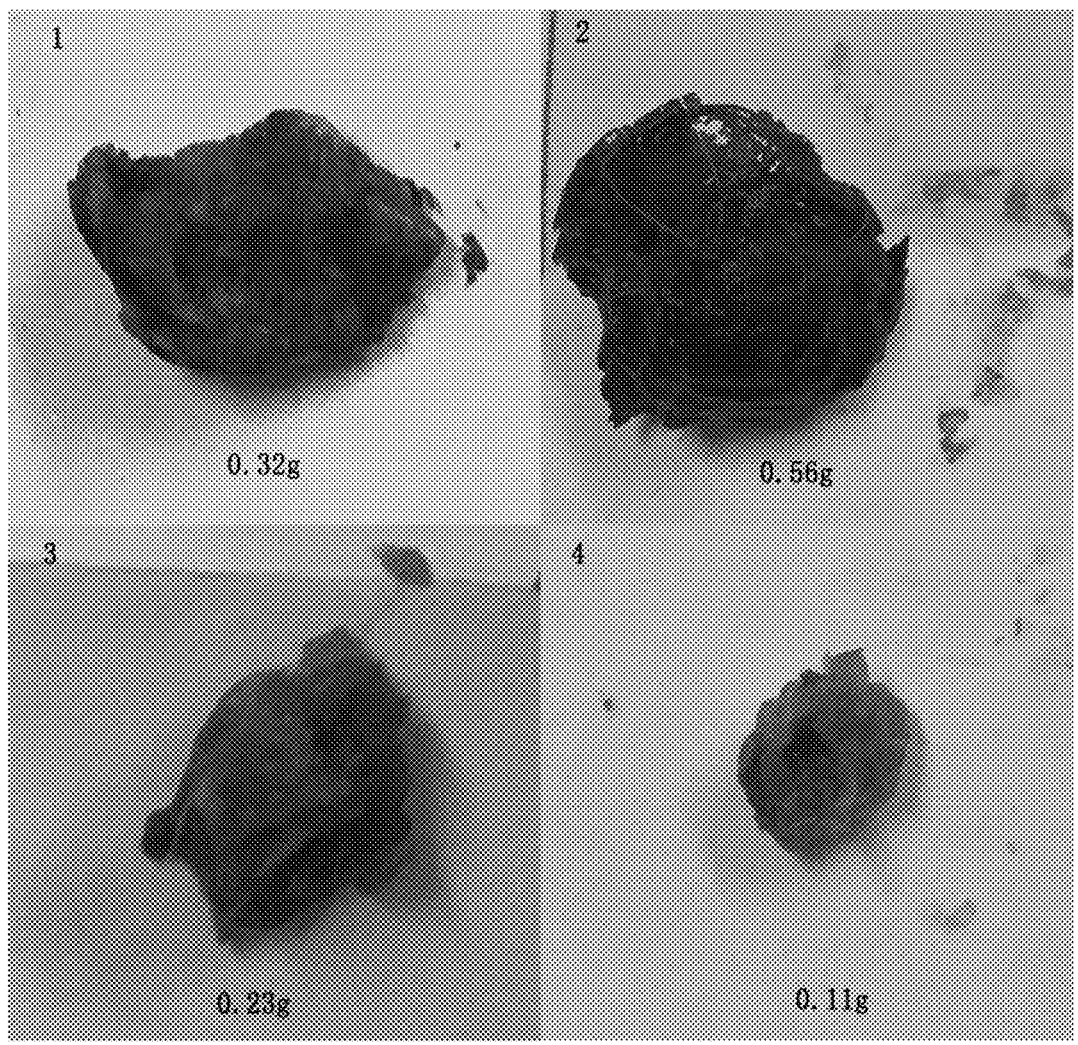

The radiological examination results were shown in FIG. 6A. The mice in the second group had obvious ectopic osteogenesis, with compact adhesion to autologous bones of mice. Further bone weighing found that, the rhBMP-2 prepared by in the present invention had better osteogenic induction activity than the other three recombinant proteins.

TABLE 2

Mouse muscle ectopic osteogenesis induced by four kinds of rhBMP-2

| Experiment Group | Amino acid sequence of rhBMP-2 | Average osteogenesis weight/g |
|---|---|---|
| 1 | 108-peptide | 0.385 |
| 2 | The present invention | 0.580 |
| 3 | 109-peptide | 0.240 |
| 4 | 115-peptide | 0.185 |

The rhBMP promotes new bone formation by inducing differentiation of undifferentiated mesenchymal cell C2C12 to form osteoblasts. The recombinant rhBMP-2 of the amino acid sequence of the present invention has a significant activity to promote the differentiation of C2C12 cells compared with the other three recombinant rhBMPs, exhibiting remarkable osteogenic activity.

The above technical solutions are merely illustrative of the preferred embodiments of the present invention, and are not to be construed as limiting the scope of the present invention. All modifications and improvements made based on the present invention are within the scope of protection of the present invention.

The contents of articles, patents, patent applications, and all other documents and electronically available information described or recited herein are hereby incorporated by reference in their entirety as if individually pointed out for reference for each publication. The applicant reserves the right to incorporate any and all materials and information from any such article, patent, patent application or other document into this application.

The invention claimed is:

1. A method for preparing a polypeptide, comprising:
   1) Providing a DNA sequence encoding recombinant human bone morphogenetic protein-2;
   2) Constructing an expression vector with the DNA sequence to transform *E. coli* host cells;
   3) Screening positive clones for culture and inducing an expression product of a target amino acid sequence of SEQ ID NO: 2;
   4) Renaturing and purifying the expression product to obtain the recombinant human bone morphogenetic protein-2;
   wherein the DNA sequence consists of SEQ ID NO: 3 and wherein the expression vector is pET28a having a T7 lac promoter.

2. The method according to claim 1, wherein a dilution method is used for renaturation in the step (4) and a final concentration of the recombinant human bone morphogenetic protein-2 in the renaturation buffer is controlled at 0.05-0.5 mg/ml.

3. The method according to claim 1, wherein a multi-step ion exchange chromatography is used for purification in step (4) and the steps are as follows:
   1) Loading the renatured recombinant human bone morphogenetic protein-2 solution onto a well-balanced strong anion column, and rinsing with an equilibration buffer A to reach a baseline after loading;
   2) Performing stepwise salt-gradient elution using an elution buffer A and collecting a main peak;
   3) Mixing the target peak solution collected from the strong anion column and loading onto a weak cation column, and rinsing with an equilibration buffer B to reach the baseline after loading; and
   4) Performing stepwise salt-gradient elution using an elution buffer B and collecting the main peak.

4. The method according to claim 3, wherein the equilibration buffer A comprises 10-50 mM Tris-HCl, 1-5 M urea, and 1%-10% mannitol, and pH of the equilibration buffer A is 8.5-8.9.

5. The method according to claim 3, wherein the elution buffer A comprises 10-50 mM Tris HCl, 1-5 M urea, 1%-10% mannitol, and 1-5 M NaCl, and pH of the elution buffer A is 8.5-8.9.

6. The method according to claim 3, wherein the equilibration buffer B comprises 10-50 mM phosphate buffer PB, 1-5M urea, and 1%-10% mannitol, and pH of the equilibration buffer B is 6.0-6.5.

7. The method according to claim 3, wherein the elution buffer B comprises 10-50 mM phosphate buffer PB, 1-5M urea, 1%-10% mannitol, and 1-5 M NaCl, and pH of the elution buffer B is 6.0-6.5.

8. The method according to claim 3, wherein the amino acid sequence is subjected to galactosylated modification.

9. The method according to claim 8, wherein the galactosylated modification is modified by artificial modification in vitro or by in vivo expression in a eukaryotic organism.

* * * * *

SEQUENCE LISTING

<160> NUMBER OF SEQ ID NOS: 6

<210> SEQ ID NO 1
<211> LENGTH: 107
<212> TYPE: PRT
<213> ORGANISM: Homo sapiens

<400> SEQUENCE: 1

```
Lys Arg Leu Lys Ser Ser Cys Lys Arg His Pro Leu Tyr Val Asp Phe
1               5                   10                  15

Ser Asp Val Gly Trp Asn Asp Trp Ile Val Ala Pro Pro Gly Tyr His
            20                  25                  30

Ala Phe Tyr Cys His Gly Glu Cys Pro Phe Pro Leu Ala Asp His Leu
        35                  40                  45

Asn Ser Thr Asn His Ala Ile Val Gln Thr Leu Val Asn Ser Val Asn
    50                  55                  60

Ser Lys Ile Pro Lys Ala Cys Cys Val Pro Thr Glu Leu Ser Ala Ile
65                  70                  75                  80

Ser Met Leu Tyr Leu Asp Glu Asn Glu Lys Val Val Leu Lys Asn Tyr
                85                  90                  95

Gln Asp Met Val Val Glu Gly Cys Gly Cys Arg
            100                 105
```

<210> SEQ ID NO 2
<211> LENGTH: 108
<212> TYPE: PRT
<213> ORGANISM: Homo sapiens

<400> SEQUENCE: 2

Met Lys Arg Leu Lys Ser Ser Cys Lys Arg His Pro Leu Tyr Val Asp
1               5                   10                  15

Phe Ser Asp Val Gly Trp Asn Asp Trp Ile Val Ala Pro Pro Gly Tyr
            20                  25                  30

His Ala Phe Tyr Cys His Gly Glu Cys Pro Phe Pro Leu Ala Asp His
        35                  40                  45

Leu Asn Ser Thr Asn His Ala Ile Val Gln Thr Leu Val Asn Ser Val
    50                  55                  60

Asn Ser Lys Ile Pro Lys Ala Cys Cys Val Pro Thr Glu Leu Ser Ala
65              70                  75                  80

Ile Ser Met Leu Tyr Leu Asp Glu Asn Glu Lys Val Val Leu Lys Asn
                85                  90                  95

Tyr Gln Asp Met Val Val Glu Gly Cys Gly Cys Arg
            100                 105

<210> SEQ ID NO 3
<211> LENGTH: 327
<212> TYPE: DNA
<213> ORGANISM: Homo sapiens

<400> SEQUENCE: 3
atgaaacgtc tgaaaagcag ctgcaaacgt cacccgctgt acgttgattt cagcgatgtt     60
ggctggaacg attggatcgt tgcgccgccg ggctaccacg cgttctactg ccacggcgaa    120
tgcccgttcc cgctggcgga tcacctgaac agcaccaacc acgcgatcgt tcagaccctg    180
gttaacagcg ttaacagcaa atcccgaaa gcgtgctgcg ttccgaccga actgtctgcg    240
atctcaatgc tgtacctgga tgaaaacgaa aagttgttc tgaaaaacta ccaggatatg    300
gttgttgaag ttgcggttg ccgttaa                                        327

<210> SEQ ID NO 4
<211> LENGTH: 115
<212> TYPE: PRT
<213> ORGANISM: Homo sapiens

<400> SEQUENCE: 4

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
    50                  55                  60

Gln Thr Leu Val Asn Ser Val Asn Ser Lys Ile Pro Lys Ala Cys Cys
65              70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
                100                 105                 110

Gly Cys Arg
        115

<210> SEQ ID NO 5
<211> LENGTH: 109

```
<212> TYPE: PRT
<213> ORGANISM: Homo sapiens

<400> SEQUENCE: 5

Met Arg Lys Arg Leu Lys Ser Ser Cys Lys Arg His Pro Leu Tyr Val
1               5                   10                  15

Asp Phe Ser Asp Val Gly Trp Asn Asp Trp Ile Val Ala Pro Pro Gly
                20                  25                  30

Tyr His Ala Phe Tyr Cys His Gly Glu Cys Pro Phe Pro Leu Ala Asp
            35                  40                  45

His Leu Asn Ser Thr Asn His Ala Ile Val Gln Thr Leu Val Asn Ser
        50                  55                  60

Val Asn Ser Lys Ile Pro Lys Ala Cys Cys Val Pro Thr Glu Leu Ser
65                  70                  75                  80

Ala Ile Ser Met Leu Tyr Leu Asp Glu Asn Glu Lys Val Val Leu Lys
                85                  90                  95

Asn Tyr Gln Asp Met Val Val Glu Gly Cys Gly Cys Arg
                100                 105

<210> SEQ ID NO 6
<211> LENGTH: 108
<212> TYPE: PRT
<213> ORGANISM: Homo sapiens

<400> SEQUENCE: 6

Met Lys Lys Leu Lys Ser Ser Cys Lys Arg His Pro Leu Tyr Val Asp
1               5                   10                  15

Phe Ser Asp Val Gly Trp Asn Asp Trp Ile Val Ala Pro Pro Gly Tyr
                20                  25                  30

His Ala Phe Tyr Cys His Gly Glu Cys Pro Phe Pro Leu Ala Asp His
            35                  40                  45

Leu Asn Ser Thr Asn His Ala Ile Val Gln Thr Leu Val Asn Ser Val
        50                  55                  60

Asn Ser Lys Ile Pro Lys Ala Cys Cys Val Pro Thr Glu Leu Ser Ala
65                  70                  75                  80

Ile Ser Met Leu Tyr Leu Asp Glu Asn Glu Lys Val Val Leu Lys Asn
                85                  90                  95

Tyr Gln Asp Met Val Val Glu Gly Cys Gly Cys Arg
                100                 105
```